(12) United States Patent
Perez-Garcia et al.

(10) Patent No.: US 7,192,925 B2
(45) Date of Patent: Mar. 20, 2007

(54) SCORPION PEPTIDE AS HYPOTENSIVE AGENT

(75) Inventors: Maria Elena de Lima Perez-Garcia, Minas Gerais (BR); Carlos Ribeiro Diniz, Minas Gerais (BR); Robson Augusto Souza Dos Santos, Minas Gerais (BR); Pierre Edouard Bougis, Marseilles (FR); Marie-France Eauclaire, Marseilles (FR); Adriano Monteiro de Castro Pimenta, Minas Gerais (BR)

(73) Assignee: Universidade Federal de Minas Gerais, Belo Horizonte (BR)

( * ) Notice: Subject to any disclaimer, the term of this patent is extended or adjusted under 35 U.S.C. 154(b) by 0 days.

(21) Appl. No.: 10/517,097

(22) PCT Filed: Jun. 9, 2003

(86) PCT No.: PCT/BR03/00073

§ 371 (c)(1),
(2), (4) Date: Jul. 6, 2005

(87) PCT Pub. No.: WO03/104274

PCT Pub. Date: Dec. 18, 2003

(65) Prior Publication Data

US 2006/0014928 A1    Jan. 19, 2006

(30) Foreign Application Priority Data

Jun. 7, 2002  (BR)  .................................... 0202157

(51) Int. Cl.
*A61K 38/17* (2006.01)
*C07K 14/435* (2006.01)

(52) U.S. Cl. ............................ 514/12; 514/13; 514/21; 530/856; 530/325; 530/324

(58) Field of Classification Search .................. 514/12, 514/13, 21; 530/856, 325, 324
See application file for complete search history.

(56) References Cited

OTHER PUBLICATIONS

Result 5 from Geneseq database search, alignment of Seq ID No.: 4 with Seq ID No.: 1839, yseF protein from *Lactococcus lactis*, Bolotine et al., FR 2807446 A1, searched on Dec. 29, 2005.*

* cited by examiner

*Primary Examiner*—Jon Weber
*Assistant Examiner*—Rosanne Kosson
(74) *Attorney, Agent, or Firm*—Caesar, Rivise, Bernstein, Cohen & Pokotilow, Ltd.

(57) ABSTRACT

The present invention provides isoformes from a peptide family belonging to South American scorpion *Tityus serrulatus* that acts as hypotensive agents by potentiating Bradykinin and, therefore, can be used as anti-hypertensive drugs. A peptide was firstly isolated from *Tityus serrulatus* venom and showed a strong and long-lasted hypotensive activity when tested in rats. This peptide was first named TsHpt-I (*Tityus serrulatus* Hypotensin-I). Also, three more highly similar isoformes were identified and revealed a peptide family with very close primary structure. They were named TsHpt-II, TsHpt-III and TsHpt-IV.

11 Claims, No Drawings

SCORPION PEPTIDE AS HYPOTENSIVE AGENT

This application is the U.S. national phase of International Application No. PCT/BR03/00073, filed on Jun. 9, 2003, which claims priority to Brazilian Application No. PI 0202157-9, filed on Jun. 7, 2002.

The present invention relates to the isolation and characterization of peptides from scorpion venom, suitable for use as pharmaceutical drugs in treatment of hypertension.

BACKGROUND

Discussion of Prior Art

About 600 million people worldwide have high blood pressure and nearly 0.5% of this total die per year as direct result of hypertension. It is well known that hypertension increases the risk of heart disease, heart attacks and strokes and yet 70% of people with hypertension are not adequately treated. According to World Health Organization (WHO) and International Society of Hypertension (ISH) it is projected that death and disability from coronary heart disease and cerebro-vascular disease are rapidly increasing in developing countries and they will be ranked on top among the causes of the global burden of disease in the next twenty years. Because of the central role played by hypertension in coronary heart disease and stroke, it is claimed by WHO-ISH that one of the biggest challenges facing public health authorities and physicians is the control of hypertension. (Bulletin of the Worl Health Organization, 1999, 77 (3).)

Blood pressure is measured as systolic, i.e. pressure of the blood in the arteries when the heart beats, and diastolic, i.e. pressure between heartbeats. Values of blood pressure are expressed in millimeters of mercury (mmHg) units. According to WHO-ISH the optimal blood pressure is less than 120 systolic and 80 diastolic, i.e., 120/80 mmHg, while normal blood pressure is classed as less than 130/85 mmHg. High blood pressure, or hypertension, is considered to be a pressure greater than or equal to 140/90 mmHg and "high normal" blood pressure is between 130/85 and 140/90 mmHg. Both hypertension and "high normal" blood pressure pose threat to health. (Bulletin of the Worl Health Organization, 1999, 77 (3).)

High blood pressure occurs when the body's smaller blood vessels (known as the arterioles) narrow, which causes the blood to exert excessive pressure against the vessel walls. The heart must therefore work harder to maintain this higher pressure. Although the body can tolerate increased blood pressure for months and even years, eventually the heart can enlarge and be damaged (a condition called hypertrophy), and injury to blood vessels in the kidneys, the brain, and the eyes can occur. Hypertension has been aptly called a silent killer, because it usually produces no symptoms (U.S. Pat. No. 6,569,891. Owen, et al. May 27, 2003).

At the present time, six classes of drugs are recognized as efficient for hypertensive treatment: diuretics, beta-blockers, angiotensin converting enzyme (ACE) inhibitors, calcium antagonists, angiotensin II antagonists and alpha-blockers. The drug of choice for a patient treatment depends on factors such as age, ethnicity and presence of others cardiovascular conditions.

Diuretics cause the body to excrete water and salt. ACE inhibitors reduce the production of angiotensin—a peptide that constricts arteries—and reduce the degradation of bradykinin—a peptide that dilates arteries. Beta-blockers block the effects of adrenaline, thus easing the heart's pumping action and widening blood vessels. Vasodilators expand blood vessels and calcium channel blockers help decrease the contractions of the heart and widen blood vessels.

Research now indicates that beta-blockers, diuretics, and ACE inhibitors all reduce the risk for fatal and non-fatal cardiovascular events. As first-line treatment experts generally recommend beta-blockers or diuretics, which are inexpensive, safe, and effective, for most people with hypertension who have no complicating problems (U.S. Pat. No. 6,569,891. Owen, et al. May 27, 2003). Combination drug therapy can be recommended for patients whose blood pressure does not fall to optimal levels with single drug treatment.

All drugs used for hypertension have side effects, some distressing, and on-going compliance is difficult. Therefore, there is still need for novel anti-hypertensive drug classes (Bralet and Schwartz, TRENDS in Pharmacological Sciences, Vol. 22 No. 3, March 2001).

Animal venoms have proved to be a valuable resource of unique and novel chemical compounds that have shown a wide variety of biological activities. Furthermore, advancements in synthetic organic chemistry have made it possible to synthesize not only newly identified natural products, but also structural analogs and semi-synthetic derivatives. Even with all the advances in synthetic organic chemistry, however, much time and effort is saved by using a model compound established through the elucidation of a novel natural product.

Isolation of natural products include, fungi, bacteria, marine organisms (sponges, snails, fishes and sea snakes) arthropods, amphibian, reptiles and the number of newly reported compounds is increasing fast. It has been estimated that more than 2,500 toxins and other natural products with biological activity have been already isolated from animal venoms (Theakston R D, Kamiguti A S. A list of animal toxins and some other natural products with biological activity. Toxicon. 2002 May; 40(5):579–651.)

Scorpion venom is a peptide rich mixture with many different biological activities and is known as one of the richest sources of biologically active peptides. This reflects millions of years in evolution of specialized venom producing glands. Scorpions are among the oldest (400 million years) living groups of animals. They are represented by 1500 distinct species and their venom is a mixture of components containing about 50–100 polypeptide toxins. Thus, about 100,000 different peptides are surmised to exist in all these species. However, only a small number of these polypeptide toxins, about 200 distinct polypeptides from 30 different species of scorpion, have been described and published to date.

Natural venoms are metabolic products not directly essential for the life of producer organism, although they are essential for both predatory and defense needs. Venom constituents can act in many fronts on the victim's tissues such as ionic channels in excitable tissues and specific receptors, like enzymes, for example, leading to disturbances in muscular, cardiovascular or respiratory systems.

The use of venoms from animal sources in prospecting new drugs candidates has increased enormously in the last decade.

The most studied and representative classes of bioactive compounds found in scorpion venoms are related to small proteins, i.e., less than 10 kDa, which bind on selective ionic channels of both invertebrates and vertebrates nervous systems. These proteins are able to block or modulate kinetics of $Na^+$, $K^+$, $Ca^{2+}$ and $Cl^-$ selective-channels, leading the inflicted victim to a massive neurointoxication and sometimes death. Due to their selectively, scorpion toxins are classified accordingly: 1) to their toxicological spectrum; 2) to their binding sites on ionic selective channels and 3) to their structural family.

However, little is known about other classes of molecules present in scorpion venom that are not lethal and causes only micro-toxicological effects.

Peptides from animal venoms that are active as bradykinin-potentiating factors are of particular interest because of their strong effect as hypotensive agent.

To date, bradykinin-potentiating factors or bradykinin-potentiating peptides have been found in venom from the spider *Lactrodectus tredecimguttatus*, from the scorpions *Leiurus quinquestriatus, Tityus serrulatus, Buthus martensii* and *B. occitanus* and from Viparidae snakes, mainly, from the southamerican genus *Bothrops* sp.

Since such agents would be vasodilators they have potential in hypertension and any disease where tissue blood perfusion is compromised. Such indications include, but are not limited to, systemic hypertension, angina, stroke, retinal vascular diseases, claudication, Raynauds disease, diabetes, and pulmonary hypertension. (U.S. Pat. No. 6,573,390, Burk, 3 Jun. 2003).

Peptides described as Bradykinin-like or as Bradykinin-potentiating factors are also active on insect nervous system and can, therefore, be envisaged as potential insecticides. Bradykinin related peptides have been found in many venoms of insects from *Hymenoptera*(ants and social wasps). Injections of these peptides into vertebrate predators may play an important role in their defense since they produce severe pain. On the other hand, Piek and co-workers, working with Bradykinin-like peptides isolated from wasp venoms, investigated the effects of these peptides on the insect central nervous system. These kinins block in a irreversibly manner, the nicotinic synaptic transmission from the cercal nerve to a giant interneuron in the sixth abdominal ganglion of the cockroach *Periplaneta americana*, by depletion of the transmitter in the presynaptic site.

SUMMARY OF THE INVENTION

Peptides that form a structural family were purified from the venom of Brazilian scorpion *Tityus serrulatus*. Structurally, this family is identifiable by the absence of Cys residues and therefore with no disulfide bonds. Moreover, mature peptides from this family ranges from 2500 to 3000 Da and have typical amino acid signatures (Pro-Pro-Ala or Pro-Pro) at their carboxi-terminal extremity. Pharmacologically, these peptides act as bradykinin-potentiating peptides, and therefore, can be used as hypotensive agents. These, structural and pharmacological features, classify members of this peptide family as serious candidates to be used as pharmaceutical drugs in the treatment of hypertension.

DETAILED DESCRIPTION OF THE INVENTION

Definitions

*Tityus serrulatus*: A Brazilian scorpion species presently classified as follows: *Eukariota; Metazoa; Arthropoda, Chelicerata; Arachnida; Scorpiones; Buthoidea; Buthidae; Tityus; Tityus serrulatus*. Since this is a parthenogenetic species, i.e., a species with an assexual reproduction in which embryos develop without any fecundation, *Tityus serrulatus* has been recently placed as an all-female morph species derived from *Tityus stigmurus*, another South American scorpion species. Moreover, a sexual population of *Tityus serrulatus* was recently put on evidence on Minas Gerais State, in Brazil.

Scorpion Venom: A secretion produced by the venom gland located at the scorpion telson. The venom constituents, mainly proteins, are produced by the gland cells and secreted into the glandular lumen. It is used in both predatory and defense senses being toxic to many animals, for example, from insects to humans. Methods of venoms extraction consist on electrical or manual milking, in which the gland content is expelled and collected for further preparations. Alternatively, the whole telson or gland is "crushed" in an organic or inorganic medium and the proteins purified from the whole telson or gland extract. Crude venom or whole venom are related to the complete milked solution without any further preparation such as lyophilization or any separation step. Soluble fraction of venom is related to the venom, preferably lyophilized venom, that was resuspended on a solution, preferably a low ionic strength buffer and submitted to centrifugation to separate the soluble fraction from the solid fraction.

Peptide: A protein with low molecular mass. Although there is not a real boundary between protein and peptide, peptides are considered, in a practical sense, as proteins smaller than 10000 Da.

Liquid chromatography: A molecular separation method consisting on a mobile phase, a solvent or a buffer, for example, passed throughout a fixed phase with particular physico-chemical properties. Molecules samples are loaded onto a cylindrical tube filled with the fixed phase and are eluted by the mobile phase being separated by means of the physico-chemical properties related to: 1) the molecules themselves; 2) the fixed phase and 3) the mobile phase. Conventional, Fast Performance Liquid Chromatography (FPLC) or High Performance (or Pressure) Liquid Chromatography (HPLC) are related to the apparatus used. Size-exclusion (or molecular filtration), Ionic (Cationic or Anionic) Exchanges and Reversed-phase (or Hydrophobicity) are related to physico-chemical properties of the fixed phase.

Inventors have made intensive and extensive studies on isolation of novel scorpion peptides from the venom gland of a scorpion *Tityus serrulatus*, on the basis of their ability to show any biological activity. As a result, the inventors have succeeded in isolation and purification of a novel peptide family, named Scorpion Hypotensive Peptides (SHptP), represented by SEQ ID NO: 1; SEQ ID NO: 2; SEQ ID NO: 3 and SEQ ID NO: 4, in which anti-hypertensive properties were found. They have also succeeded in determination of the primary and higher-order structures of TsHpt-I (SEQ ID NO: 1). It has been found that native and synthetic TsHpt-I (SEQ ID NO: 1) exhibits strong ability to decrease blood pressure in rats. Thus, the invention has been accomplished.

This invention is related to a family of peptides, which will be referred to as Scorpion Hypotensive Peptides (SHptP), found in scorpion venom, which have common structural and pharmacological features. The structural and pharmacological features that can be used in this peptides family identification are listed:

i) Lack of Cystein residues and, therefore, no internal disulfide bridges;

ii) A molecular signature at the C-terminal ending or portion, described as: Xaa-Pro-Pro and Xaa-Pro-Pro-Ala, where Xaa is any amino acid residue;

iii) pairs of amino acid residues such as Pro-Pro, Lys-Glu, Lys-Asp, Arg-Glu, Arg-Asp, Ile-Ile, Ile-Leu, Leu-Leu, Leu-Ile, which form a protective shield against amino-, endo- and carboxi-proteinases enzymes;

iv) Hypotensive effects using "in vivo" tests (bioassays) in vertebrates.

Native peptides, with structural and anti-hypertensive properties described above, were found in the venom of the Brazilian scorpion *Tityus serrulatus*, after fractionation of the crude venom using liquid chromatography.

Animals were collected in the Minas Grais State, Brazil, and their venom was collected by electrical stimulus. Alternatively, manual stimulus can also be applied with the same result.

In a preferred manner, venom was dialysed against distilled water to eliminate salts and small peptides. After gel filtration through Sephadex G-50, samples of interest were loaded preferably onto a reverse-phase HPLC column, equilibrated with a polar acidic solvent, preferably 0.1% TFA in water (solvent A) and eluted using a gradient of a apolar solvent, preferably 0.1% TFA in acetonitrile (solvent B). The elution was measured at 230 nm and 280 nm. Collected samples was then submitted to MALDI-TOF mass spectrometry analyses. Fractions of interest were further purified, using a shallower gradient of solution B, preferably using the same reverse-phase column.

Purified peptides, as judged by reversed phase HPLC profile and mass spectrometry analyses were submitted to further investigation in order to determine their primary structure. Two main molecular species, measuring 2652.25 Da and 2724.64 Da, were identified by MALDI-TOF mass spectrometry analyses and subjected to amino acid hydrolysis and subsequent analysis, and amino acid sequencing by automated Edman's degradation. The sum of these analyses, i.e., I-IPLC chromatographic profiles, MALDI-TOF mass spectrometry, amino acid hydrolysis and analysis and amino acid sequencing by Edman's degradation, led us to identify four isoformes molecules belonging to the same structural family that were named: TsHpt-I (*Tityus serrulatus* Hypotensin-I), TsHpt-II (*Tityus serrulatus* Hypotensin-II), TsHpt-III (*Tityus serrulatus* Hypotensin-III) and TsHpt-IV (*Tityus serrulatus* Hypotensin-IV), identified by the referred sequences SEQ ID NO: 1; SEQ ID NO: 2; SEQ ID NO: 3 and SEQ ID NO: 4.

All of the four molecules described here are linear polypeptide chains without any Cys residues and, therefore, without any internal disulfide bridge. TsHpt-I and TsHpt-II are composed of 25 amino acid residues, being the sole difference between these two chains, the amino acid in position 15, which is a Gln residue in TsHpt-I and a Glu residue in TsHpt-II. The other two molecules found, i.e., TsHpt-III and TsHpt-IV are composed of 24 amino acid residues differing from TsHpt-I and TsHpt-II by the absence of the C-terminal residue Ala. TsHpt-III and TsHpt-IV differ one from the other by the same mutation that was observed for TsHpt-I and TsHpt-II, i.e., a shift in the residue at position 15, which is a Gin in TsHpt-III sequence and a Glu in the TsHpt-IV sequence.

Peptides of the present invention, belonging to the Scorpion Hypotensive Peptides (SHptP) family, can be isolated from scorpion venoms. They may also be synthesized, chemically or by recombinant techniques from the isolated gene encoding the peptide or its preprotein or from a synthetic or cDNA copy of the gene.

Variants, i.e. isoformes, of the peptides of the present invention may be prepared synthetically by peptide synthesis techniques, recombinantly or by cleavage from an isolated peptide of the invention, as in the case of TsHpt-III and TsHpt-IV.

Similar polypeptides can be produced by conventional site-directed mutagenesis, which is one avenue for routinely identifying residues of the molecule that can be modified without rendering the resulting polypeptide biologically inactive, or by chemical synthesis.

Nucleotides sequences encoding peptides or variants of the peptides of the present invention are also within the scope of this invention. Insect viruses and plants may be engineered to express the peptides and/or variants in a manner to render themselves as vectors, vehicles or excipients for the peptides to another organism.

It is well-known that there is substantial redundancy in the various codons which code for specific amino acids. Therefore, this invention is also directed to those DNA sequences which contain alternative codons which code the identical amino acid. For purposes of this specification, a sequence having one or more replaced codons will be defined as a degenerate variation. Also included within the scope of this invention are variations in the DNA sequence which do not alter the ultimate physical properties of the expressed protein. (U.S. Pat. No. 5,494,895, Garcia, et al., 27 Feb. 1996).

This invention also concerns chemical modification of the peptides of the present invention. Although native peptides described by this invention did not show any post-translational modification as, for instance, acetylation, deamidation, pyroglutamic acid formed from Gln, C-terminal amide formed from Gly, methylation, phosphorylation, and others, such modifications of the native, synthetized or recombinant peptides may be achieved. These modifications may be important to protect peptides from enzymatic degradation leading to an extended half-life of peptides used as drugs.

This invention also concerns the anti-hypertensive properties of Scorpion Hypotensive Peptides (SHptP) family and the application of peptides belonging to SHptP family as hypotensive agents in pharmaceutical applications for hypertension treatments and purposes.

TsHpt-I were found to be able to potentiate bradykinin effects in a strong and long-lasting manner.

Bioassays using waked and anesthetized rats showed that the potentiating unit of TsHpt-I was 10 μg. At this dose TsHpt-I was able to double the activity of a single dose of bradykinin for almost 20 minutes in anesthetized animals.

EXAMPLES

While the foregoing specification teaches the principles of the present invention, with examples provided for the purpose of illustration, it will be understood that the practice of the invention encompasses all of the casual variations, adaptations, modifications, deletions or additions of procedures and protocols described herein, as come within the scope of the following claims and its equivalents. Therefore, it is to be understood that the present invention is not limited to the examples.

Example 1

Fractionation of *Tityus serrulatus* Venom and Purification of Peptides

Venom of *Tityus serrulatus* scorpion, captured in the wild, in the Minas Gerais State, Brazil, or raised in the laboratory, preferably soluble fraction, is used to isolation of peptides belonging to TsHpt family.

Fractionation of the venom is carried out on a liquid chromatography system preferably as follows: soluble fractions are submitted to a dialysis against distilled water (24 h, 4° C., 1 liter×5, using Spectrapor 3 membrane with a mol. wt. cut-off<1000). After, the dialyzed solution is recovered and applied onto a conventional size-exclusion (Superdex G50) liquid chromatography system and eluted with water and acetic acid. Alternatively, venom can be fractionated directly on a HPLC or FPLC system using reverse-phase C4 or C18 column. The yield is separated in different pools according to the separation profile. Peptides with molecular mass in the range of 2000 to 3000 are normally found spread out in all collected pooled fractions.

Further purification of peptides is carried out preferably on HPLC system with a reverse-phase C4 or C18 column and eluted by a gradient using a non-polar solvent. Mobile phases (solutions) are preferably: A) Trifluoroacetic acid (TFA) 0.1%, v/v, in pure grade water and B) TFA 0.1%, v/v in Acetonitrile. Lyophilyzed samples are dissolved in solution A and load onto column (RP-C 18) using a solution A flow at 1 mL/minute, preferably. Gradient is achieved by introducing solution B, preferably at 0.01 to 1% by minute. Elution profile is monitored by absorbance at 210–230 nm. Proteins eluted can also be monitored by mass spectrometry analyses. Alternatively ionic changes columns can be used using any liquid chromatography system.

Commonly, fraction III, issued from previously Sephadex® G50 was loaded (575 ?g) onto a reverse-phase HPLC column (Merk 100 RP-18, 4×250 mm, Lichrospher, 5?m), equilibrated with 0.1% TFA (solvent A) and eluted (1.0 ml/min) in gradient of solvent B (0.1% TFA in acetonitrile) using a ratio of 0.33% B/min. The elution was measured at 230 nm and 280 nm. Collected samples (1.0 ml each) was then submitted to MALDI-TOF analysis. Fractions of interest were found at a retention time between 72 to 91 minutes and were further purified, using a shallower gradient (0.1% B/min) at the same reverse-phase column.

Example 2

Chemical Characterization of Peptides—Determination of Structure of Peptides

After isolation from semi-purified fractions, two samples containing: i) a peptide with an observed molecular mass of 2652.25 Da and ii) a peptide with an observed molecular mass of 2724.64 Da were submitted to amino acid analysis and sequencing as described: Lyophilized samples (1 nmol) were submitted to acidic hydrolysis under $N_2$ atmosphere at 110° C. by 24 or 72 hours using a Pico-Tag™ work-station (Millipore/Waters Associates). After hydrolysis, samples were analyzed on a Beckman 6300 apparatus. To amino acid sequencing, native peptides (1 nmol) were submitted to Edman automated sequencing using an Applied Biosystems 476 A sequencer.

MALDI-TOF mass spectrometry analyses were performed on a Voyager-DE™RP BioSpectrometer Workstation (Perseptive Biosystems, Framingham, Mass., USA) in the positive linear mode. Protein solutions (0.5 µL of sample, variable concentrations) were spotted onto the target, followed by 0.5 µL of CHCA (α-cyano-4-hydroxycinnamic acid) matrix solution (60% acetonitrile/0.3% TFA), and allowed to dry at room temperature (dried-droplet method). A 337 nm nitrogen laser was used to desorb the samples. Mass spectra were obtained from the average of 256 laser pulses from m/z 600 to 39,400. In MALDI-TOFMS experiments, external calibration of the mass scale was performed using a standard polypeptide mixture (Sequazyme Peptide Mass, Perseptive Biosystems). Known toxins from *Tityus serrulatus* venom were also used in some cases as standard references for internal multipoint calibration. Data processing was performed with the GRAM/386 software.

Edman degradation of peptide with molecular mass of 2652.25 Da showed a linear peptide with 24 residues, without any C residues. The calculated monoisotopic mass for the sequence obtained from automated Edman's degradation was 2652.40 Da. Sequencing of peptide with an observed molecular mass of 2724.64 Da showed the same sequence as the previously described peptide, except for the additional Ala residua at C-terminus and for the position 15, in which two different residues (Gln and Glu) were identified. This mutation, i.e. Gln to Glu, leads to a 1 Da difference that could not be distinguishable on both HPLC and mass spectrometry analyses. The calculated molecular mass varied from 2723.44 Da, in the Gln15 isoform, to 2724.42 Da in the Glu isoform and mass spectrometry analyses showed an observed mass of 2724.64 Da.

Example 3

Circular Dichroism (CD) Analyses of TsHpt-I

The CD spectra aquisitions were performed in a JOBIN-IVON CD6, with λ178–260 and an analysis time of 30 seconds/nm, ∈1 mm.

Samples of TsHpt-I (200 µg) were diluted in 200 µL of pure grade water, phosphate buffer 50 mM, or in different concentrations of trifluoroethanol (TFE) as follows: 12.5, 25, 50 and 90%.

Spectra showed that this peptide secondary structure is predominantly random coiled. Increasing in band at 220 nm in solutions of higher concentrations of TFE indicates that an alpha-helix structure can be formed at hydrophobic environment.

Example 4

The peptide related to the invention, TsHpt-I, could also be obtained by FMOC chemical synthesis. The TsHpt-I obtained has the same chromatographic properties as the native molecule. The mass measured of the synthetic peptide was 2723.12 Da and is very similar to the calculated monoisotopic mass of 2723.44 Da. The synthetic molecule has the same hypotensive activity as the native molecule as assessed by biological assays on rats.

Example 5

Biological Activity Data—Anti-Hypertensive Properties of Scorpion Hypotensive Peptides (SHptP) Family Wistar rats, weighting 300±20 g were used, waked or anesthetized, to assess the hypotensive properties of peptides. Bradykinin (Bachem, Co) and TsHpt-I were dissolved in sterile isotonic saline (0.9% NaCl) immediately before use.

"In vivo" experiments using waked animals: a day before the experiment, rats were anesthetized with ether and a polyethylene catheter (PE-10 connected to PE-50) was inserted into the abdominal aorta through the femoral artery for blood pressure measurements. For intravenous injections, a polyethylene cannula was implanted into the femoral vein. Arterial blood pressure and heart rate were monitored by a solid-state strain-gauge transducer. All variables were recorded continuously on a computer through a data acquisition system, Biopac®, and processed by the Acknowledge® software.

Bradykinin, 1 µg or 2 µg, was injected and the response measured as variation on average arterial pressure. Hypotensive effect of TsHpt-I (10 µg) alone was measured after Bradykinin. The hypotensive effect of bradykinin (1 µg) was then re-evaluated after 5 and 10 minutes following the injection of TsHpt-I.

"In vivo" experiments using anesthetized rats: the arterial blood pressure and heart rate were monitored continuously after insertion of catheters as described above. Rats were previously anesthetized with urethane, 1.2 mg/kg, (via i.p.).

The hypotensive effect of intravenous injections of bradykinin, 1 µg or 2 µg was measured, followed by the measurement of hypotensive effect of TsHpt-I (10 µg). The hypotensive effect of the bradykinin (1 µg) was then re-evaluated after 1, 5, 10, 15, 20 and 30 minutes.

The potentiating unit—i.e., the amount of peptide that is able to double the activity of a single dose of bradykinin—of TsHpt-I was 10 µg. At this dose TsHpt-I was able to double the activity of a single dose of bradykinin for almost 20 minutes in anesthetized animals.

Therefore, this invention provides the possibility of using new molecules and formulations to treat hypertension.

These peptides, and their possible variants, are small, relatively simple and inexpensive to construct and can help to enlarge the knowledge and the use of peptides as medicaments.

While the above description contains many specificities, these should not be construed as limitations on the scope of the invention, but rather as an exemplification of one preferred embodiment thereof.

Other variations are possible such as, for example, the use of bradykinin-potentiation peptides in sinergy with bradykinin-like peptides that act on insect nervous system to envisage a new biological insecticide.

Another example is related to genetically engineered virus, microorganisms and plants to be used as vectors, vehicles or excipients for the peptides to another organism, for drug administration or insecticidal purposes.

Genes encoding the hypotensive effective peptides according to the present invention can be introduced into a plant by genetic engineering techniques, which upon production of the peptide in the plant cell is expected to be useful as a means for administrable drug. Therefore, it is possible to use a plant cell as excipient or vector.

It is necessary, however, that the genetic sequence coding for the peptide be expressed and produced as a functional peptide in the resulting plant cell or modified organism. It is believed that DNA from both genomic DNA and cDNA and synthetic DNA encoding an effective peptide may be used for transformations. Further, a gene may be constructed partially of a cDNA clone, partially of a genomic clone or partially of a synthetic gene and various combinations thereof. In addition, the DNA coding for a peptide gene may comprise portions from various species other than from the source of the isolated peptide.

Methods to produce virus, microorganisms and plants expressing foreign genes are known. (U.S. Pat. No. 5,441,934, Krapcho, et al., 15 Aug. 1995)

Accordingly, the scope of the invention should be determined not by the embodiments illustrated, but by the appended claims and their legal equivalents.

The invention claimed is:

1. An isolated or synthetic peptide comprising a member selected from the group consisting of: SEQ ID NO: 1; SEQ ID NO: 2; SEQ ID NO: 3 and SEQ ID NO: 4, wherein the peptide is an anti-hypertensive agent.

2. The peptide of claim 1, wherein the peptide is produced by recombinant techniques using a viral system, a bacterial system, a fungal system, other prokaryotic systems, other eukaryotic systems or a combination thereof.

3. A method for producing an administrable pharmaceutical composition comprising the peptide of claim 1, comprising the step of combining the peptide of claim 1 with a pharmaceutically acceptable carrier.

4. A pharmaceutical composition comprising an anti-hypertensive amount of the peptide of claim 1.

5. A method for chemically modifying the peptide of claim 1, comprising the step of acetylating, deamidating, methylating or phosphorylating the peptide of claim 1.

6. The peptide of claim 1, wherein the peptide is expressed in a venom of a scorpion.

7. The peptide of claim 1, wherein the peptide comprises at least two features selected from the group consisting of:

i) a lack of cysteine residues and a lack of internal disulfide bridges; ii) a molecular signature at a C-terminal ending or portion, described as: Xaa-Pro-Pro or Xaa-Pro-Pro-Ala, where Xaa is any amino acid residue; iii) pairs of amino acid residues effective to form a protective shield against amino-, endo- and carboxi-proteinase[s] enzymes; and iv) hypotensive effects in vertebrates.

8. The peptide of claim 1, wherein the peptide is free of cysteine residues and internal disulfide bridges.

9. The peptide of claim 1, wherein the peptide comprises a molecular signature at a C-terminal ending or portion, described as: Xaa-Pro-Pro or Xaa-Pro-Pro-Ala, where Xaa is any amino acid residue.

10. The peptide of claim 1, wherein the peptide comprises pairs of amino acid residues effective to form a protective shield against amino-, endo- and carboxi-proteinases enzymes.

11. The peptide of claim 1, wherein the peptide has a hypotensive effect in vertebrates.

* * * * *

SEQUENCE LISTING

<160> NUMBER OF SEQ ID NOS: 4

<210> SEQ ID NO 1
<211> LENGTH: 25
<212> TYPE: PRT
<213> ORGANISM: Tityus serrulatus

<400> SEQUENCE: 1

Ala Glu Ile Asp Phe Ser Gly Ile Pro Glu Asp Ile Ile Lys Gln Ile
1               5                   10                  15

Lys Glu Thr Asn Ala Lys Pro Pro Ala
            20                  25

<210> SEQ ID NO 2
<211> LENGTH: 25
<212> TYPE: PRT
<213> ORGANISM: Tityus serrulatus

<400> SEQUENCE: 2

Ala Glu Ile Asp Phe Ser Gly Ile Pro Glu Asp Ile Ile Lys Glu Ile
1               5                   10                  15

Lys Glu Thr Asn Ala Lys Pro Pro Ala
            20                  25

```
<210> SEQ ID NO 3
<211> LENGTH: 24
<212> TYPE: PRT
<213> ORGANISM: Tityus serrulatus

<400> SEQUENCE: 3

Ala Glu Ile Asp Phe Ser Gly Ile Pro Glu Asp Ile Ile Lys Gln Ile
1               5                   10                  15

Lys Glu Thr Asn Ala Lys Pro Pro
            20

<210> SEQ ID NO 4
<211> LENGTH: 24
<212> TYPE: PRT
<213> ORGANISM: Tityus serrulatus

<400> SEQUENCE: 4

Ala Glu Ile Asp Phe Ser Gly Ile Pro Glu Asp Ile Ile Lys Glu Ile
1               5                   10                  15

Lys Glu Thr Asn Ala Lys Pro Pro
            20
```